(12) United States Patent
Stevens et al.

(10) Patent No.: US 9,161,822 B2
(45) Date of Patent: Oct. 20, 2015

(54) CONFORMANCE MODEL

(75) Inventors: Randal A. Stevens, Elk River, MN (US); Roger A. Neilson, Jr., Zimmerman, MN (US)

(73) Assignee: In'Tech Industries, Inc., Maple Grove, MN (US)

( * ) Notice: Subject to any disclaimer, the term of this patent is extended or adjusted under 35 U.S.C. 154(b) by 2089 days.

(21) Appl. No.: 12/324,532

(22) Filed: Nov. 26, 2008

(65) Prior Publication Data

US 2010/0128033 A1    May 27, 2010

(51) Int. Cl.
G06T 15/00 (2011.01)
A61C 1/08 (2006.01)
A61C 13/00 (2006.01)
A61C 9/00 (2006.01)

(52) U.S. Cl.
CPC ............ *A61C 1/084* (2013.01); *A61C 13/0004* (2013.01); *A61C 13/0013* (2013.01); *A61C 9/004* (2013.01)

(58) Field of Classification Search
CPC .............. A61C 1/084; A61C 13/0013; A61C 13/0004; A61C 9/004
USPC ............. 345/418, 419, 420, 629; 433/75, 76, 433/213, 219; 382/131
See application file for complete search history.

(56) References Cited

U.S. PATENT DOCUMENTS

| | | | |
|---|---|---|---|
| 5,320,529 A | 6/1994 | Pompa | |
| 5,514,519 A | 5/1996 | Neckers | |
| 5,575,656 A * | 11/1996 | Hajjar | 433/219 |
| 5,768,134 A | 6/1998 | Swaelens et al. | |
| 9,746,814 | 6/2004 | Coe | |
| 7,329,122 B1 | 2/2008 | Scott | |
| 7,774,084 B2 * | 8/2010 | Cinader, Jr. | 700/119 |
| 7,785,104 B2 * | 8/2010 | Scott | 433/75 |
| 7,824,181 B2 * | 11/2010 | Sers | 433/76 |
| 7,887,327 B2 * | 2/2011 | Marotta | 433/213 |
| 2007/0160953 A1 | 7/2007 | Tardieu | |
| 2008/0124676 A1 | 5/2008 | Marotta | |

FOREIGN PATENT DOCUMENTS

WO    WO 2005/053564 A2    6/2005

OTHER PUBLICATIONS

Holmberg et al (A Non-Animal Alternative for Teaching Introductory Surgery, Humane Innovations and Alternatives 1994;8:635-637.*

(Continued)

*Primary Examiner* — Phu K Nguyen
(74) *Attorney, Agent, or Firm* — Brooks, Cameron & Huebsch, PLLC (57) ABSTRACT

Among various methods, systems, and apparatuses, a number of methods are provided for forming a 3D conformance model of a particular portion of a subject's anatomy using 3D digitized imaging data and a rapid prototyping technique. One such a method includes distinguishing at least one particular structural feature associated with the exterior of the particular portion from at least one particular structural feature associated with the interior of the particular portion. Such a method can include using the conformance model to test suitability of an appliance to participate in performing an intended function that includes penetrating the interior of the particular portion through the exterior of the particular portion.

11 Claims, 3 Drawing Sheets

(56) References Cited

OTHER PUBLICATIONS

"Brontes from 3M." Nov. 26, 2008. 1 pg. http://www.youtube.com/watch?v=V5pQquGLQfY.

"3M ESPE Evolves the Lava Brand Evolves to Become the Company's Global Digital Resoratives Brand." Press Release. Sep. 24, 2008. 4 pgs. http://solutions.3m.com/wps/p . . . .

"3Shape A/S—3D Scanner and CAD/CAM software." Nov. 26, 2008. 24 pgs. http://www.3shape.com/.

"WaterShed XC 11122 Receives USP Class VI Approval." Posted on Jan. 1, 2009. (cont. in next box). http://www.timecompression.com/products/watershed-xc-11122-receives-usp-class-vi-approval.aspx. Accessed on Jan. 20, 2009. 1 pg.

AccuDental. "CT Scanning Protocol." http://www.medicalmodeling.com/accudental/images/AccuDental_CT_Protocol.pdf. Jan. 23, 2009. 4 pgs.

International Search Report and Written Opinion from related PCT Application No. PCT/US2009/006285, dated Jul. 15, 2010. 16 pgs.

\* cited by examiner

CONFORMANCE MODEL

TECHNICAL FIELD

The present disclosure relates to the field of rapid prototyping and, in particular, to using three-dimensional digital imaging in combination with rapid prototyping to form a conformance model.

BACKGROUND

Rapid prototyping is the automated construction of physical objects using solid freeform fabrication. Techniques for rapid prototyping became available in the late 1980s and have been used, for instance, to produce models and prototype parts. Rapid prototyping later became useful for a broader range of applications including, in some instances, making production quality parts in relatively small numbers. As an illustration, some sculptors have used rapid prototyping technologies for producing objects having complex shapes for fine art exhibitions.

In some instances, rapid prototyping may take three-dimensional (3D) modeling from computer-aided design (CAD) software and transform such modeling into thin, horizontal, virtual cross-sections. Such virtual cross-sections may then be formed sequentially in physical space until a complete physical representation of an intended object has been created using one or more of a number of rapid prototyping techniques.

Implementation of various rapid prototyping techniques may enable additive fabrication where an appropriate apparatus reads CAD data input and lays down successive layers of liquid, powder, and/or sheet material to build up the intended object in a series of physical cross-sections. These physical cross-sections, which correspond to the virtual cross-sections of the CAD modeling, may be joined together, fused, and/or cured to create the intended physical object.

Stereolithography is an example of rapid prototyping technology that may be used to produce physical objects having accuracy and a good surface finish. An apparatus capable of performing stereolithography may be referred to as a Stereolithography Apparatus (SLA).

DETAILED DESCRIPTION OF THE DISCLOSURE

Among various methods, systems, and apparatuses, a number of methods are provided for forming a three-dimensional (3D) conformance model of a particular portion of a subject's anatomy using 3D digitized imaging data and a rapid prototyping technique. In various embodiments, such a method includes distinguishing at least one particular structural feature associated with the exterior of the particular portion of the subject's anatomy from at least one particular structural feature associated with the interior of the particular portion of the subject's anatomy. Such a method can, in various embodiments, include using the conformance model to test suitability of an appliance to participate in performing an intended function that includes penetrating the interior of the particular portion of the subject's anatomy through the exterior of the particular portion of the subject's anatomy. In various embodiments, such a method can include acquiring and saving 3D digitized imaging data representing exterior and interior structural features of the particular portion of the subject's anatomy.

Traditional injection molding, for instance, may be less expensive for manufacturing polymer products in high quantities. However, additive fabrication using rapid prototyping techniques may be faster and less expensive when producing small quantities of physical objects. For example, forming a one-off model of a portion of a subject's anatomy to assist in planning and/or performing treatment of a medical or dental condition can be accomplished more quickly and with less cost and/or effort on the part of a user (e.g., physician, prosthodontist, orthodontist, technician, among others) and/or the subject (e.g., a patient) as compared to using other techniques, such as injection molding, among other techniques.

A number of rapid prototyping technologies that utilize additive fabrication are available. An underlying variable in such technologies is the manner by which cross-sectional layers are added to form the physical object. Alternative rapid prototyping technologies can include, but are not limited to: stereolithography using a SLA that utilizes a vat of a photopolymer that is curable by exposure to light (e.g., a particular wavelength range and/or intensity of such light) and a suitable light source (e.g., a laser) to form solid physical objects a layer at a time by selectively curing the photopolymer by appropriately directing the light exposure; selective laser sintering (SLS) using a high power laser to fuse small particles (e.g., a powder) of plastic, metal, and/or ceramic into a solidified 3D object; laminated object manufacturing (LOM) using thin layers of a solid material (e.g., paper, plastic, metal, among others) that are cut to shape (e.g., using a high power laser) and sequentially stacked and bonded together; and electron beam melting (EBM) of titanium alloys.

Additional rapid prototyping technologies that utilize additive fabrication include: fused deposition modeling (FDM) using a plastic filament or metal wire (e.g., various thermoplastics, eutectic metals, among others) that are unwound from a coil and supplied to an extrusion nozzle that can control the flow and heat the material to melting point in order to lay down such material in layers; and 3D printing (3DP) using sequential layers of a fine powder (e.g., plaster, corn starch, and/or resins, among others) that are either selectively bonded by "printing" an adhesive (possibly along with a colorant) from a number of inkjet-type printheads in the shape of each cross-section or "printing" a liquid (e.g., a photopolymer, possibly along with a colorant) through the ink-jet type printheads that is curable by exposure to light as it is deposited; among other possible additive fabrication rapid prototype techniques.

Microelectromechanical systems (MEMS) can, when appropriate, be utilized in combination with or instead of the just-described rapid prototyping technologies. MEMS can be made from components between 1-100 micrometers in size and may include a central unit that processes data (e.g., a microprocessor) and several components that interact with outside elements (e.g., a polymer) through micro-focused release of energy (e.g., electrons, heat, light, and the like). With advancements in research and manufacturing, MEMS technology may become more miniaturized so as to merge into the nano-scale to produce nanoelectromechanical systems (NEMS).

In some instances, MEMS technology may be utilized in combination with Huntsman MicroLightSwitch® (MLS) technology, which can enable a large surface area of a radiation-curable resin (e.g., a photopolymer) to be selectively exposed in a single step via a micromechanical shutter system in order to reduce processing time (e.g., compared to sequentially directed laser light exposures). An alternative technology to overcome a limited speed of, for instance, laser scanning is to utilize a digital micro-mirror device (DMD) for digital light processing (e.g., DLP® from Texas Instruments) in order to direct light to more than one location simultaneously or nearly simultaneously.

A photopolymer can be a liquid or semi-liquid polymer that can be "cured" to become solid when exposed to a particular intensity and/or wavelength range of light, for instance, in the ultraviolet (UV) spectrum. Examples of commercially available photopolymers include DuPont Cyrel®, BASF Nyloflex®, OMNOVA Solutions NovaCryl™, and Rbcor Elaslon™, among others. Such photopolymers can be used to form solid objects when exposed to light of appropriate intensity and/or wavelength range (e.g., as directed by STereoLithography (STL) file formatting) in a rapid prototyping apparatus (e.g., SLA, 3DP, among other such apparatuses). A number of photopolymers, as described elsewhere in the present disclosure, can display a range of different colors, textures, and/or other distinguishing indicators when "overcured."

A photopolymer can be a photopolymerizable material that is curable by directed exposure to electromagnetic radiation that produces photochemical reactions. Electromagnetic radiation that can produce photochemical reactions can be called actinic radiation. Actinic radiation can be provided by a variety of sources, for instance, lasers (e.g., which may have a high power and/or a narrow wavelength output), X-ray tubes, infrared (IR) lamps, UV fluorescent tubes, mercury vapor lamps (e.g., which may have low, medium, or high pressure), argon glow lamps, photographic flood lamps, pulsed xenon lamps, carbon arc lamps, among other light sources.

By way of example and not by way of limitation, the actinic radiation can be directed UV light at a wavelength of approximately 365 nanometers (nm). Unexposed and/or unpolymerized regions of the photopolymer can be removed by a solvent and the polymerized and solidified regions can be subsequently dried. In some situations, also by way of example and not by way of limitation, the solidified region of the formed object can be detackified by exposure to 254 nm UV light and/or further hardened by exposure to additional exposure to 365 nm UV light.

Figure 1A:
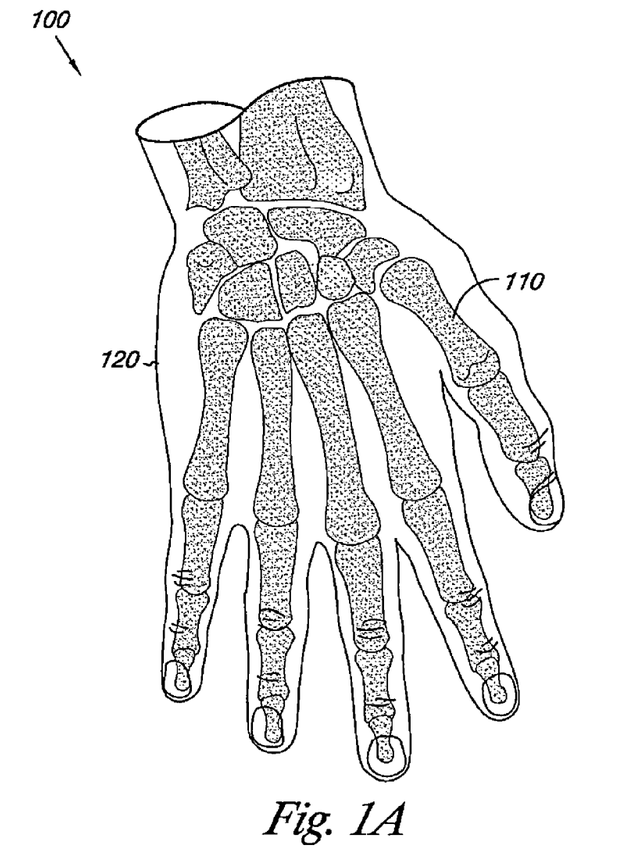
FIG. 1A illustrates a perspective view of a representative three-dimensional (3D) conformance model that can be formed in accordance with one or more embodiments of the present disclosure.

FIG. 1A illustrates a perspective view of a representative 3D conformance model that can be formed in accordance with one or more embodiments of the present disclosure. FIG. 1A shows an example of a 3D conformance model 100 embodiment, in this example a hand (e.g., a human hand), formed consistent with the teachings of the present disclosure. The conformance model 100 illustrates one of a number of possible configurations for a representation of a hand formed with rapid prototyping technologies (e.g., SLA) consistent with the teachings of the present disclosure.

In contrast to most other previously described techniques (e.g., the 3Shape A/S Dental Designer™ and various associated 3D scanners, the 3M ESPE/Brontes Lava™ Chairside Oral Scanner, among others) that display surface contours, rapid prototyping techniques can, as described in the present disclosure, be used to form physical objects having interior structural features and exterior structural features that are distinguishable and that correspond to acquired and saved 3D digitized imaging data obtained from scanning the particular portion of the subject's anatomy. By way of example and not by way of limitation, rapid prototyping techniques can utilize digital (e.g., computerized) data obtained from axial tomography (CT) scanning of a subject's dental arch to form a physical model of the subject's dental arch where structural features associated with the interior of the dental arch (e.g., a bone, a cavity, a pocket, and/or a sinus, among other such features) are formed in such a manner as to be distinguished from structural features associated with the exterior of the dental arch (e.g., teeth and/or gingiva, among other such features).

An STL file format is a data interface between CAD software and various apparatuses utilized for rapid prototyping. An STL file approximates the shape of an object to be physically reproduced from the CAD cross-sectional representation using triangular facets. In implementations practiced prior to the present disclosure (e.g., the 3Shape and 3M ESPE/Brontes products), a single STL file for each scanned object typically described only the surface geometry of the 3D object without representations of interior structural features, especially as distinguished from exterior structural features by different colors, textures, and/or other distinguishing indicators.

As described in the present disclosure, a photopolymer can be "overcured" by directed exposure to a particular additional intensity of and/or a different wavelength range of actinic radiation. Such overcuring can cause particular regions of the photopolymer to display one or more characteristics that distinguish such regions from "ordinarily cured" regions. Overcuring of particular regions of some photopolymers can result in display of different colors, textures, and/or other distinguishing indicators in comparison to the ordinarily cured regions of such photopolymers. Examples of such photopolymers include: Huntsman Advanced Materials KenShape® resins (e.g., SL YC-9300); DSM Somos® resins; 3D Systems Accura® SL materials; Dreve FotoTec® SL materials; and Ciba-Geigy Corporation SL epoxy resins; among a number of other types of photopolymer resins.

The amount of energy that initiates polymerization (e.g., bonding) of a photopolymer may be referred to as the critical energy. An additional amount of energy may be supplied to photopolymer resins (e.g., those just described) to induce display the one or more characteristics that distinguish such regions from the ordinarily cured regions (e.g., different colors, textures, and/or other distinguishing indicators). By way of example and not by way of limitation, application of a larger amount of laser energy (e.g., around 5-100 times) to a particular region of the photopolymer than the critical energy that caused resin polymerization can overcure the desired region so as to affect the optical density immediately.

In some circumstances, a photopolymer can be overcured by initial application, also by way of example and not by way of limitation, of an amount of laser energy that is not as far above the critical energy (e.g., around 1.1-5.0 times). Causing the particular region of the photopolymer that has been exposed to such energy to display the changed optical density (e.g., different colors, textures, and/or other distinguishing indicators) can be accomplished by subsequent exposure of the whole photopolymer (including the region that has been exposed to more than the critical energy) to an elevated temperature for an appropriate time period. A model as described in the present disclosure can, for example, be placed in an oven and heated (e.g., to around 50-100 degrees Celsius). The period of time for such heating can depend upon the characteristics of the model (e.g., the type of photopolymer used, the size of the model, and/or the amount of laser energy exposure, among other factors). The changes in optical density (e.g., different colors, textures, and/or other distinguishing indicators) in the particular overcured region can become expressed, apparent, and/or visible (e.g., displayed) during and after such heating.

In some instances, the overcuring can cause such distinguishing characteristics to be displayed by, for instance, inducing a photochemical reaction and/or heating of one or more regions of the photopolymer, as directed by the STL file, to induce a color, shading, and/or texture change, among other possible inducible distinguishing characteristics. In some instances, as an alternative or in addition to the photochemical reaction and/or heating of the photopolymer, the photopolymer can include a number of photoresponsive agents that, in response to the overcuring exposure to the particular additional intensity of and/or the different wavelength range of the actinic radiation, as directed by the STL file, can display a distinguishing color, shading, and/or texture change, among other possible inducible distinguishing characteristics. In other instances, overcuring the photopolymer, as directed by the STL file, can remove or reduce a color and/or shading (e.g., by photobleaching the photopolymer and/or the photoresponsive agent) to induce a distinguishing color and/or shading.

As described in the present disclosure, forming a conformance model can, in some embodiments, include using a SLA and a plurality of STL files to form the conformance model. The conformance model can, in various embodiments, be formed such that the at least one structural feature associated with the interior of the particular portion of the subject's anatomy displays a particular color that is visible through the at least one structural feature associated with the exterior of the particular portion of the subject's anatomy.

In various embodiments, a conformance model can be formed using a 3D scanning apparatus, in various embodiments, to scan an exterior and an interior of a particular portion of a subject's anatomy. Such a 3D scanning apparatus can be configured to scan the exterior and the interior of the particular region of the subject's anatomy using one or more scanning technologies, where the scanning technologies can include at least one of X-ray radiographics, computerized axial tomography (CT), nuclear magnetic resonance (NMR), and positron emission tomography (PET), among other comparable technologies.

A plurality of STL files can be utilized to record 3D digitized imaging data, where at least one particular structural feature associated with the exterior of the particular portion of the subject's anatomy is stored in a first STL file and at least one particular structural feature associated with the interior of the particular portion of the subject's anatomy is stored in a second STL file. A SLA, in some embodiments, can be interfaced with the plurality of STL files, where the SLA differentially cures particular regions of a photopolymer of the conformance model as defined by at least the first STL file and the second STL file.

The differential cure of the photopolymer can, in various embodiments, result in production or removal of a first color for the first structural feature associated with the exterior of the particular portion of the subject's anatomy and production of a second color for the second structural feature associated with the interior of the particular portion of the subject's anatomy. In some embodiments, the first color associated with the exterior can result from ordinarily curing the photopolymer in order that such a region can be approximately transparent and/or colorless, in particular when compared to the second color associated with the interior.

The differential cure of the photopolymer can result from directed exposure to light of particular regions of the photopolymer corresponding to at least a first structural feature stored in the first STL file and at least a second structural feature stored in the second STL file. Such light can be selected from a group that includes different total intensities of light of a particular wavelength range (e.g., as defined by the wavelength output of the light source and/or the light sensitivity of the photopolymer and/or photoresponsive agent) to which the particular portions of the photopolymer are exposed, at least two different wavelength ranges (e.g., as defined by differential, largely non-overlapping wavelength ranges emitted by two light sources, for example, lasers), and/or a combination of the different total intensities of light of the particular wavelength range and the at least two different wavelength ranges. In various embodiments, the total intensities of light can be measured in units such as candelas, footcandles, lumens, lux, and the like.

In various embodiments, more than one color can be produced such that each color can be associated with a different structural feature of two or more structural features in the interior of the particular portion of the subject's anatomy. Similarly, in various embodiments, more than one color can be produced such that each color can be associated with a different structural feature of two or more structural features on the exterior of the particular portion of the subject's anatomy.

The 3D scanning apparatus can be configured, in various embodiments, to scan the exterior and the interior of the particular region of the subject's anatomy using one or more scanning technologies. As described above, such scanning technologies can include at least one of X-ray radiographics, computerized axial tomography (CT), nuclear magnetic resonance (NMR), and positron emission tomography (PET), as appreciated by one of ordinary skill in the relevant art, among other comparable technologies. Such a 3D scanning apparatus can, in some embodiments, be configured to scan within the subject's oral cavity to distinguish hard and soft tissue associated with an exterior region of a dental arch (e.g., teeth, gingival tissue, and the like) from hard and soft tissue associated with an interior region of the dental arch (e.g., a bone structure, cavities, pockets, and/or sinuses, and the like).

The conformance model 100 illustrated in FIG. 1A shows an embodiment of a hand (e.g., a human hand) formed to have a bone structure 110 associated with the interior of the hand visually displayed by a color that distinguishes the bone structure 10 from the soft tissue 120 (e.g., skin, muscle, tendons, and the like) that is associated with the exterior of the hand. In some embodiments, such as the hand shown in FIG. 1A, the conformance model 100 can have at least one portion of the photopolymer (e.g., structures associated with the exterior) be substantially transparent and/or translucent (e.g., be absent of color and/or shading or have a pale color and/or shading). In such embodiments, structures associated with the interior can, for example, display a different color and/or be more opaque (e.g., have a different color, shading and/or texture) than the exterior structures such that the interior structures can be visually distinguished through and from such exterior structures.

Figure 1B:
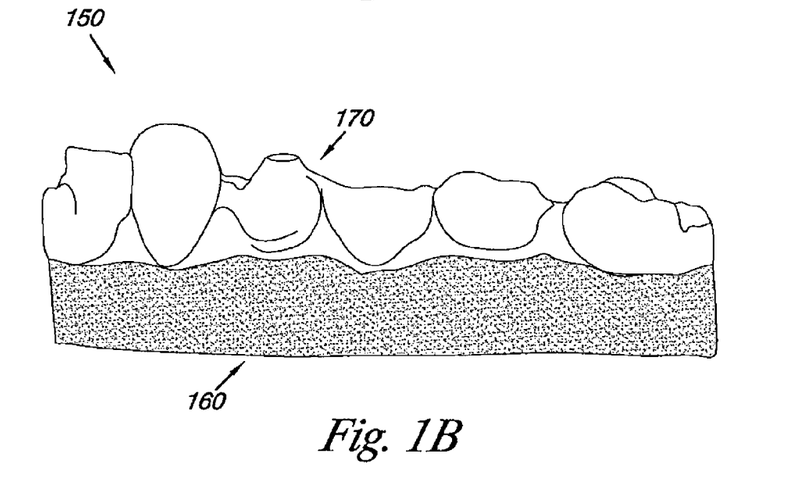
FIG. 1B illustrates a perspective view of another representative 3D conformance model that can be formed in accordance with one or more embodiments of the present disclosure.

FIG. 1B illustrates a perspective view of another representative 3D conformance model that can be formed in accordance with one or more embodiments of the present disclosure. The conformance model 150 illustrated in FIG. 1B shows an embodiment of a dental arch (e.g., a human dental arch) formed to have a bone structure 160 associated with the interior of the dental arch visually display a color that distinguishes the bone structure 160 from the tissue 170 (e.g., gingiva, teeth, and the like) that is associated with the exterior of the dental arch. As described with regard to FIG. 1A, in some embodiments, such as the dental arch shown in FIG. 1B, the conformance model 150 can have at least one portion of the photopolymer, from which structures associated with the exterior are formed, be substantially transparent and/or translucent (e.g., be absent of color and/or shading or have a pale color and/or shading) such that structures associated with the interior that, for example, display a different color and/or are more opaque (e.g., have a different color, shading and/or texture) can be visually distinguished through and from such exterior structures.

In conformance models that include interior bone structures, such as the dental arch shown in FIG. 1B, the interior structure that can be made distinguishable by differential color, shading, and or texture can, in some embodiments, be one or more cavities, pockets, and/or sinuses associated with the bone structure. In some embodiments, the bone structure can be made distinguishable from the cavities, pockets, and/or sinuses and, in addition, each of these interior structures can be made distinguishable from exterior structures, for example, by each displaying different colors, shading, and/or textures. The number of different colors, shading, and/or textures achievable in conformance models is not limited by the previous description.

Various systems incorporating a number of elements of the present disclosure in various configurations may be utilized. In various embodiments, a memory device can store instructions on hardware (e.g., an application-specific integrated circuit), firmware, and/or software memory to be executed, in some embodiments, by a processor (e.g., of a computer). By way of example and not by way of limitation, embodiments of the present disclosure can be utilized in a processor-based system that includes, among other components, a processor and a memory device coupled to the processor. For example, such a memory device and processor can, in some embodiments, be coupled to a 3D scanning apparatus and a SLA. The plurality of STL files utilized to record 3D digitized imaging data can, in some embodiments, be functionally associated with the processor and the memory device coupled to the processor to serve as the data interface between CAD software and various apparatuses (e.g., the SLA) utilized for rapid prototyping.

The memory device can, in various embodiments, include a memory structure, where the memory structure includes instructions for executing performance of acquiring 3D digitized imaging data representing exterior and interior structure of a particular portion of a subject's anatomy. Such a memory device can be used for storing the 3D digitized imaging data in the plurality of STL files, where at least one particular structural feature associated with the exterior of the particular portion is stored in a first STL file and at least one particular structural feature associated with the interior of the particular portion is stored in a second STL file. In various embodiments, the memory device and/or the processor can participate in creating a digital 3D conformance model using at least the first and second STL files by distinguishing the at least one particular structural feature associated with the exterior of the particular portion of the subject's anatomy from the at least one particular structural feature associated with the interior of the particular portion of the subject's anatomy.

The memory structure can, in various embodiments, also include instructions for executing performance of using imaging data representing at least one structural feature stored in the first STL file that is different from at least one structural features stored in the second STL file. For example, the morphology, contours and/or internal details of the gingiva and/or teeth associated with the exterior of a subject's dental arch can be stored in the first STL file and the morphology, contours, and/or internal details of the bone structure, tooth roots, cavities, pockets, and/or sinuses associated with the interior of the subject's dental arch can be stored in the second STL file.

Additionally, the memory structure can, in various embodiments, also include instructions for executing performance of interfacing the plurality of STL files with a SLA for differentially curing particular regions of a photopolymer of a physical conformance model being formed, where the differential curing is defined by at least the first STL file and the second STL file. As described herein, the differential cure of the photopolymer can, in various embodiments, result from directed exposure to light of particular regions of the photopolymer corresponding to at least a first structural feature stored in the first STL file and at least a second structural feature stored in the second STL file.

Hence, the differential curing can include using the first STL file and the second STL file for directing differential application of light to the photopolymer. Such differential curing can, in various embodiments, result in at least producing or removing a first color for a first structural feature associated with the exterior of the particular portion of the subject's anatomy and at least producing a second color for a second structural feature associated with the interior of the particular portion of the subject's anatomy. As described herein, exposing particular regions of the photopolymer corresponding to at least a first structural feature stored in the first STL file and at least a second structural feature stored in the second STL file to light can be performed with light selected from a group that includes: different total intensities of light of a particular wavelength range; at least two different wavelength ranges; and/or a combination of the different total intensities of light of the particular wavelength range and the at least two different wavelength ranges.

The conformance model 150 illustrated in FIG. 1B can be formed by utilizing a rapid prototyping apparatus (e.g., a SLA) that creates at least one color boundary to distinguish at least two types of tissue. In various embodiments, such a conformance model 150 can be used to test whether the configuration of a dental appliance is suitable to perform an intended function. In the present disclosure, the term "dental appliance" is intended to encompass instrumentalities configured to at least assist in dental (e.g., prosthodontic and/or orthodontic) treatment of a subject's dental arch. For example, in some embodiments, the conformance model 150 can be used to test the suitability of the configuration of a dental drill guide to properly assist in performing insertion of a dental implant.

Figure 2:
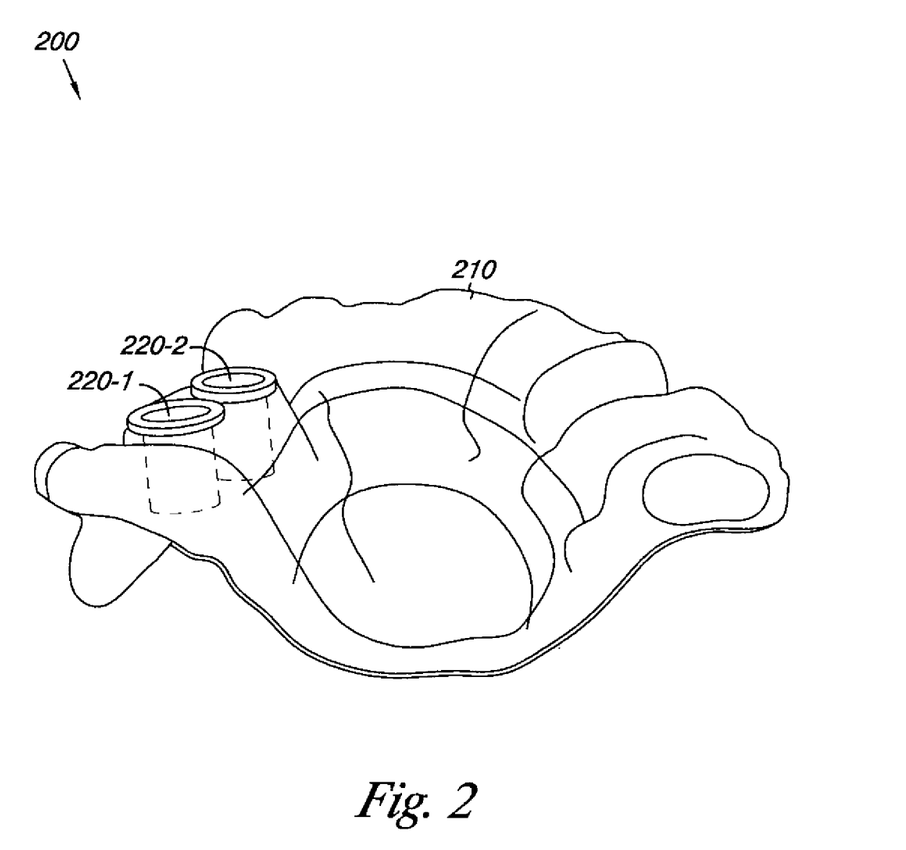
FIG. 2 illustrates a perspective view of an appliance that can be tested with a 3D conformance model in accordance with one or more embodiments of the present disclosure.

FIG. 2 illustrates a perspective view of an appliance that can be tested with a 3D conformance model in accordance with one or more embodiments of the present disclosure. FIG. 2 illustrates a dental appliance 200 with a body 210 that can be conformal to the external contours of a subject's dental arch and/or surrounding tissue. The body 210 can, in various embodiments, include one or more drill guides positioned to assist in accurately aiming insertion and/or progress of a drill bit while, for example, preparing for insertion of a dental implant. The embodiment illustrated in FIG. 2 shows the body 210 as having two such drill guides 220, however, embodiments of the present disclosure are not so limited.

Preparation of a dental appliance can, in some embodiments, include forming a cast (e.g., using silicon and/or other appropriate material) on a conformance model, for example, a portion of or the entire conformance model 150 of the dental arch illustrated in FIG. 1B. Such a cast of a targeted region can, in various embodiments, be digitally scanned, converted into one or more STL files, and physically formed utilizing a rapid prototyping apparatus (e.g., a SLA).

A resultant dental appliance, for example, with one or more drill guides already formed and/or subsequently inserted into the dental appliance, can have the configuration tested for suitability to assist in performing drilling as intended into one or more targeted locations in the underlying tissue (e.g., a portion of a bone structure). Such a test can be performed, in various embodiments, by fitting the dental appliance onto the conformance model, as described in the present disclosure, and testing the configuration of such a dental appliance in properly performing the intended function. For example, the configuration of a drill guide can be tested utilizing one or more techniques as described below.

Figure 3:
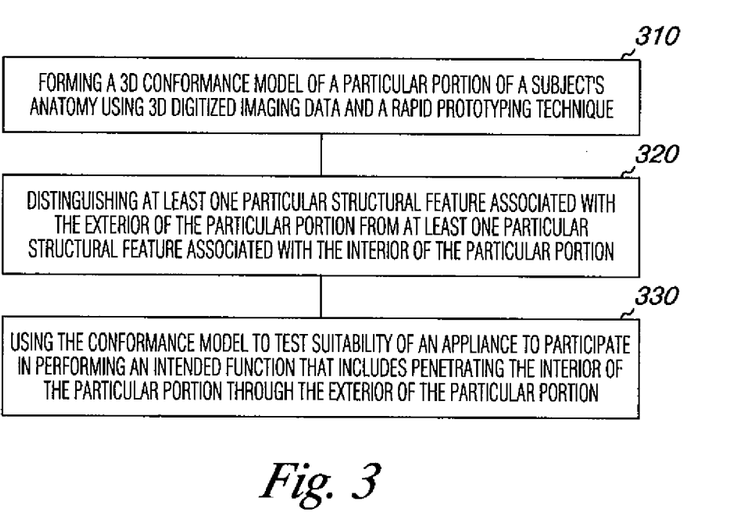
FIG. 3 is a block diagram illustrating forming a 3D conformance model according to one or more method embodiments of the present disclosure.

FIG. 3 is a block diagram illustrating forming a 3D conformance model according to one or more method embodiments of the present disclosure. Unless explicitly stated, the method embodiments described herein are not constrained to a particular order or sequence. Additionally, some of the described method embodiments, or elements thereof, can occur or be performed at the same, or at least substantially the same, point in time.

The embodiment illustrated in FIG. 3 includes forming a 3D conformance model of a particular portion of a subject's anatomy using 3D digitized imaging data and a rapid prototyping technique, as shown at block 310 and as described herein. In various embodiments, 3D digitized imaging data representing exterior and interior structural features of the particular portion of the subject's anatomy can be acquired and/or saved.

As shown in block 320, the method includes distinguishing at least one particular structural feature associated with the exterior of the particular portion from at least one particular structural feature associated with the interior of the particular portion, as described herein. In various embodiments, the conformance model can be formed such that the at least one structural feature associated with the interior of the particular portion displays a particular color that is visible through the at least one structural feature associated with the exterior of the particular portion. In some embodiments, forming the conformance model can be performed using a SLA and a plurality of STL files to physically form the conformance model.

Block 330 shows that the conformance model can be used to test suitability of an appliance to participate in performing an intended function that includes penetrating the interior of the particular portion through the exterior of the particular portion. In some embodiments, the conformance model can be used in dental treatment for testing suitability of a dental appliance to participate in performing an intended function. Such a dental appliance, as appreciated by one of ordinary skill in the relevant art, can be selected from a group that includes: a drill guide; a coping; a crown; a cap; a pontic; an inlay; a bridge; a bridge abutment; a bridge framework; an implant; an implant abutment; an implant bridge; an implant bar; and/or arrangements for anchoring such dental appliances in hard tissue and soft tissue of a dental arch of the subject.

Some embodiments of the present disclosure can include visually ascertaining whether the dental appliance is properly configured to perform the intended function with respect to at least one particular structural feature associated with an exterior of a particular dental arch and at least one particular structural feature associated with an interior of the particular dental arch. By way of example and not by way of limitation, a drill guide can be anchored to a position on the conformance model of the dental arch for which the drill guide was designed to fit and the configuration of the drill guide can be visually examined with respect to the exterior and interior of dental arch. Such a visual examination can be performed to check whether the positioning and design of the drill guide enables the drill guide to perform the intended function for which the drill guide was designed.

For example, a user can, in some embodiments, look through a bore hole in the drill guide, see through the transparent or translucent exterior (e.g., gingiva) of the conformance model of the dental arch, and ascertain whether the bore hole is appropriately aimed at a distinctly colored interior structure (e.g., a location on the jawbone). In addition, or in the alternative, a drill bit can be inserted into the bore hole of the drill guide anchored to the conformance model and the drill bit can be used to bore a tunnel into the conformance model. Such a tunnel can be visually examined through the transparent or translucent exterior of the conformance model of the dental arch to ascertain whether the tunnel has reached the distinctly colored interior structure that was intended as a target.

In addition, some embodiments of the present disclosure can include objectively ascertaining whether the dental appliance is properly configured to perform the intended function with respect to at least one particular structural feature associated with an exterior of a particular dental arch and at least one particular structural feature associated with an interior of the particular dental arch. By way of example and not by way of limitation, a drill guide can be anchored to a position on the conformance model of the dental arch for which the drill guide was designed to fit and the configuration of the drill guide can be objectively examined with respect to the exterior and interior of dental arch to check whether the positioning and design of the drill guide enables the drill guide to perform the intended function for which the drill guide was designed.

For example, a user can, in some embodiments, utilize a device for physical examination of the positioning of the drill guide with respect to the interior and exterior structures on the conformance model of the dental arch. Among a number of ways of physically examining whether the drill guide is properly configured, as appreciated by one of ordinary skill in the relevant art, a light source can be aimed through the bore hole of the anchored drill guide to ascertain whether the created beam illuminates a distinctly colored interior structure that is intended as a target. Whether the beam hits or misses the intended target can be determined visually by the user and/or objectively with a light measurement device that detects physical reflection, transmission, and/or refraction of the beam by the distinctly colored interior structure that is intended as a target. In addition, or in the alternative, a drill bit can be inserted into the bore hole of the drill guide anchored to the conformance model and the drill bit can be used to bore a tunnel into the conformance model. In some embodiments, tailings from the tunnel (e.g., residue removed while drilling the tunnel) can be visually and/or objectively (e.g., physically) examined to ascertain whether the tunnel has reached the distinctly colored interior structure (e.g., by measurement of characteristics indicative of the tailings exhibiting the distinct color of the intended target).

Ascertaining whether the dental appliance is properly configured to perform the intended function can include using the drill guide and determining a physical outcome of using the drill guide, as described above by way of example and not by way of limitation. As such, determining the physical outcome of using the drill guide can include determining whether a tunnel bored by a drill bit has reached an intended target, where the intended target is the at least one particular structural feature associated with the interior of the particular dental arch.

In addition, or in the alternative, determining the physical outcome of using the drill guide can include determining whether the tunnel bored by the drill bit has reached an unintended target where the unintended target is the at least one particular structural feature associated with the interior of the particular dental arch. Determining whether the tunnel bored by the drill bit has reached the unintended target can include determining whether the tunnel bored by the drill bit has penetrated the unintended target. By way of example and not by way of limitation, the unintended target can be selected from a group that includes a cavity, a pocket, and/or a sinus in the interior of the particular dental arch.

Testing suitability of an appliance to perform an intended function using a conformance model can have a number of possible outcomes when such an appliance fails to properly perform the intended function. By way of example and not by way of limitation, testing of a drill guide can reveal that the drill guide is improperly configured (e.g., with a bore hole that is incorrectly aimed) such that a drilled tunnel would not and/or does not reach the intended target. In addition, or alternatively, testing of the drill guide can reveal that the drill guide is improperly configured such that the drilled tunnel may reach an unintended target.

As a consequence, corrective actions can be performed with regard to the appliance before the appliance has been utilized for the intended purpose (e.g., for a medical and/or dental procedure). By way of example and not by way of limitation, adjustments with regard to anchoring arrangements for a dental appliance (e.g., a drill guide) can be performed to correct for the detected misconfiguration. In addition, or in the alternative, the dental appliance can be replaced with another dental appliance determined to be more properly configured through testing with the same and/or a replacement conformance model.

As described in the present disclosure, one or more apparatuses can, in various embodiments, be utilized to form a system including 3D digitized imaging data of an exterior and an interior of a particular portion of a subject's anatomy, and a plurality of STL files to record the 3D digitized imaging data, where at least one particular structural feature associated with the exterior of the particular portion is stored in a first STL file and at least one particular structural feature associated with the interior of the particular portion is stored in a second STL file. The system can include a 3D conformance model of the particular portion of the subject's anatomy, where at least one structural feature associated with an interior of the particular portion displays a particular color that is visible through at least one structural feature associated with the exterior of the particular portion. In some embodiments, the system can, in various embodiments, include an appliance to be tested on the conformance model to ascertain whether the appliance is properly configured to perform an intended function with respect to the at least one structural feature associated with the interior of the particular portion and the at least one structural feature associated with the exterior of the particular portion.

As further described in the present disclosure, the system can include, in various embodiments, an apparatus (e.g., a SLA) that forms the 3D conformance model by a rapid prototyping technique. Such an apparatus can, in various embodiments, be interfaced with the plurality of STL files and differentially cure particular regions of a photopolymer of the conformance model as defined by at least the first STL file and the second STL file. The differential cure of the photopolymer as defined by the second STL file can, in various embodiments, produce the particular color that is visible through the at least one structural feature associated with the exterior of the particular portion as defined by the first STL file.

Although specific embodiments have been illustrated and described herein, those of ordinary skill in the relevant art will appreciate that an arrangement calculated to achieve the same results can be substituted for the specific embodiments shown. This disclosure is intended to cover all adaptations or variations of various embodiments of the present disclosure.

Reference is made to various specific embodiments in which the disclosure may be practiced herein. These embodiments are described with sufficient detail to enable those skilled in the art to practice the disclosure. It is to be understood, however, that changes may be implemented to structural, logical, and methodological components to achieve the same results and still remain within the teachings of the present disclosure.

It is to be further understood that the above description has been made in an illustrative fashion, and not a restrictive one. Combination of the above embodiments, and other embodiments not specifically described herein, will be apparent to those of ordinary skill in the relevant art upon reviewing the above description.

The applicability of the various embodiments of the present disclosure includes other applications in which the above apparatuses, devices, systems, and methods are used, for example, in implementations other than dental applications. Therefore, the applicability of various embodiments of the present disclosure should be determined with reference to the appended claims, along with the full range of equivalents to which such claims are entitled.

In the foregoing Detailed Description, various features are grouped together in a single embodiment for the purpose of streamlining the disclosure. This method of disclosure is not to be interpreted as reflecting an intention that the disclosed embodiments of the present disclosure need to use more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

We claim:

1. A method comprising:
    forming a three-dimensional (3D) conformance model of a particular portion of a subject's anatomy using 3D digitized imaging data and a rapid prototyping technique;
    distinguishing in the conformance model at least one particular structural feature associated with the exterior of the particular portion from at least one particular structural feature associated with the interior of the particular portion; and
    using the conformance model to test suitability of an appliance to participate in performing an intended function that includes penetrating the interior of the particular portion through the exterior of the particular portion of the conformance model.

2. The method of claim 1, wherein the method includes acquiring and saving 3D digitized imaging data representing exterior and interior structural features of the particular portion of the subject's anatomy.

3. The method of claim 2, wherein forming the conformance model includes using a stereolithography apparatus (SLA) and a plurality of STL files to form the conformance model.

4. The method of claim 1, wherein the method includes forming the conformance model such that the at least one structural feature associated with the interior of the particular portion displays a particular color that is visible through the at least one structural feature associated with the exterior of the particular portion.

5. The method of claim 4, wherein the method includes using the conformance model in dental treatment for testing suitability of a dental appliance to participate in performing an intended function, wherein the dental appliance is selected from a group that includes:
- a drill guide;
- a coping;
- a crown;
- a cap;
- a pontic;
- an inlay;
- a bridge;
- a bridge abutment;
- a bridge framework;
- an implant;
- an implant abutment;
- an implant bridge;
- an implant bar; and
- arrangements for anchoring such dental appliances in hard tissue and soft tissue of a dental arch of the subject.

6. The method of claim 5, wherein the method includes visually ascertaining whether the dental appliance is properly configured to perform the intended function with respect to at least one particular structural feature associated with an exterior of a particular dental arch and at least one particular structural feature associated with an interior of the particular dental arch.

7. The method of claim 5, wherein the method includes objectively ascertaining whether the dental appliance is properly configured to perform the intended function with respect to at least one particular structural feature associated with an exterior of a particular dental arch and at least one particular structural feature associated with an interior of the particular dental arch.

8. The method of claim 6 or 7, wherein ascertaining whether the dental appliance is properly configured to perform the intended function includes using the drill guide and determining a physical outcome of using the drill guide.

9. The method of claim 8, wherein determining the physical outcome of using the drill guide includes determining whether a tunnel bored by a drill bit has reached an intended target, wherein the intended target is the at least one particular structural feature associated with the interior of the particular dental arch.

10. The method of claim 8, wherein determining the physical outcome of using the drill guide includes determining whether a tunnel bored by a drill bit has reached an unintended target, wherein the unintended target is the at least one particular structural feature associated with the interior of the particular dental arch.

11. The method of claim 10, wherein determining whether the tunnel bored by the drill bit has reached the unintended target includes determining whether the tunnel bored by the drill bit has penetrated the unintended target, wherein the unintended target is selected from a group that includes a cavity, a pocket, and a sinus in the interior of the particular dental arch.

* * * * *